(12) United States Patent
Masson

(10) Patent No.: US 12,234,302 B2
(45) Date of Patent: Feb. 25, 2025

(54) CHITOSAN DERIVATIVES AND METHODS FOR PREPARING THE SAME

(71) Applicant: Primex ehf., Fjallabyggd (IS)

(72) Inventor: Mar Masson, Reykjavik (IS)

(73) Assignee: PRIMEX EHF, Fjallabyggd (IS)

(*) Notice: Subject to any disclaimer, the term of this patent is extended or adjusted under 35 U.S.C. 154(b) by 204 days.

(21) Appl. No.: 18/057,825

(22) Filed: Nov. 22, 2022

(65) Prior Publication Data

US 2023/0151121 A1 May 18, 2023

Related U.S. Application Data

(62) Division of application No. 17/270,237, filed as application No. PCT/IS2019/050009 on Aug. 23, 2019, now Pat. No. 11,535,684.

(30) Foreign Application Priority Data

Aug. 23, 2018 (IS) .......................................... 050236

(51) Int. Cl.
C08B 37/08 (2006.01)
A61K 31/722 (2006.01)

(52) U.S. Cl.
CPC .......... *C08B 37/003* (2013.01); *A61K 31/722* (2013.01)

(58) Field of Classification Search
CPC ............................. C08B 37/003; A61K 31/722
See application file for complete search history.

(56) References Cited

U.S. PATENT DOCUMENTS

| | | | |
|---|---|---|---|
| 4,436,731 A | 3/1984 | Maltz | |
| 4,772,689 A | 9/1988 | Lang et al. | |
| 4,772,690 A | 9/1988 | Lang et al. | |
| 4,985,410 A | 1/1991 | Conti | |
| 6,306,835 B1* | 10/2001 | Daly | C11D 3/48 424/407 |
| 2014/0107329 A1 | 4/2014 | Gagnon | |
| 2016/0263232 A1 | 9/2016 | Amighi et al. | |

FOREIGN PATENT DOCUMENTS

| | | |
|---|---|---|
| CN | 106167532 A | 11/2016 |
| EP | 0249779 A1 | 12/1987 |
| WO | 2012171125 A1 | 12/2012 |
| WO | 2014142757 A1 | 9/2014 |

OTHER PUBLICATIONS

Muslim, T. et al "Synthesis and bioactivities of ply(ethylene glycol)-chitosan hybrids" Carbohyd. Polym., vol. 46, pp. 323-330. (Year: 2001).*
Benediktsdottir, B. et al "N-alkylation of highly quaternized chitosan derivatives . . . " Eur. J. Pharm. Biopharm., vol. 86, pp. 55-63. (Year: 2014).*
Written Opinion and Search Report in International Application No. PCT/IS2019/050009. Dec. 19, 2019.
Search Report in Iceland Application No. 050236. Jan. 18, 2018.
Kulkarni et al. "N,N,N-Trimethyl chitsan: an advanced polymer with myriad of opportunities in nanomedicine", Carbohydrate Polymers, vol. 157, pp. 875-902. Abstract only. Feb. 10, 2017.
Benediktsdottir et al. "Synthesis of N,N,N-trimethyl chitosan homopolymer and highly substituted N-alkyl-N,N-dimethyl chitosan derivatives with the aid of di-tert-butyldimethylsilyl chitosan", Carbohydrate Polymers, vol. 86, issue 4, pp. 1451-1460. Abstract only. Oct. 15, 2011.
Xu et al. "Synthesis, characteristic and antibacterial activity of N,N,N-trimethyl chitosan and its carboxymethyl derivatives", Carbohydrate Polymers, vol. 81, issue 4, pp. 931-936. Abstract only. Jul. 23, 2010.
Sajomsang, "Synthetic Methods and Applications of Chitosan Containing Pyridylmethyl Moiety and Its Quaternized Derivatives: A Review", Carbohydrate Polymers, vol. 80, pp. 631-647. 2010.
Sieval et al., "Preparation and NMR characterization of highly substituted N-trimethyl chitosan chloride," Carbohydrate Polymers, 36:157-165, 1998.
Runarsson et al., "N-selective 'one pot' synthesis of highly N-substituted trimethyl chitosan (TMC)," Carbohydrate Polymers, 74:740-744, 2008.

* cited by examiner

*Primary Examiner* — Layla D Berry

(74) *Attorney, Agent, or Firm* — Heslin Rothenberg Farley & Mesiti P.C.

(57) ABSTRACT

Disclosed is a method of preparing N-alkylated chitosan derivatives by treating chitosan with an acid and subsequently reacting the chitosan with an alkylating agent in the presence of a base. Also provided are novel N-alkylated chitosan derivatives.

5 Claims, 7 Drawing Sheets

CHITOSAN DERIVATIVES AND METHODS FOR PREPARING THE SAME

CROSS REFERENCE TO RELATED APPLICATIONS

This application is a division of U.S. application Ser. No. 17/270,237 filed Feb. 22, 2021, and published as US20210253745A1 on Aug. 19, 2021, which is a U.S. National Phase filing under 35 U.S.C. § 371 of International Application PCT/IS2019/050009, filed Aug. 23, 2019, and published as WO 2020/039463 A1 on Feb. 27, 2020. PCT/IS2019/050009 claims priority from Iceland application number 050236, filed Aug. 23, 2018. The entire contents of each of these prior applications are hereby incorporated herein by reference.

FIELD

The invention relates to methods of preparing derivatives of chitosan. The invention further relates to chitosan derivatives.

INTRODUCTION

Chitosan is a linear polysaccharide derived from chitin, an abundant natural polymer, found in the exoskeleton of crustaceans, insects and anthropoids and in fungal cell wall. It is mostly derived from marine sources such as shrimp, lobster and crab shells. Chitosan is the deacetylated form of chitin. Full deacetylation of chitin results in chitosan with a degree of deacetylation of 100%, and has the general formula

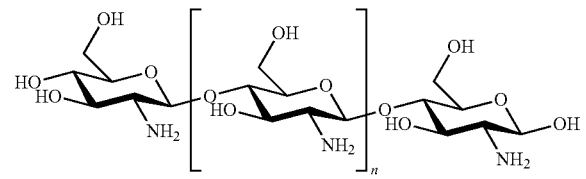

where the D-glucosamine subunits are linked by 3-(1-4) bonds. In many instances, however, deacetylation is not 100%, resulting in a chitosan polymer that consists of D-glucosamine and N-acetyl glucosamine monomers, with varying degree of deacetylation. Chitosan is a commercial product that has versatile applications in several industries. This includes its use as a hydrating compound in cosmetics, as foods preservative, as stabilizer, as food supplement, environmental friendly packaging and dietary fiber, wound healing agent in pharmaceutical application, as drug delivery system as well as several other promising applications (M. Kong, et al., Int. J. Food Microbiol., 144 (2010) 51-63).

Trimethylchitosan (N,N,N-trimethylchitosan, TMC) is a chitosan derivative with number of interesting biological applications and the advantage of high solubility independent of pH and strong antimicrobial effect and potential as absorption enhancer. Although unmodified chitosan can also have antimicrobial effect and function as absorption enhancer its effectiveness is limited to low pH (<6) due to the lack of solubility.

Trimethylchitosan is typically synthesized by reacting chitosan with a methylating agent (typically Methyl iodide (MeI) or dimethyl sulfonate (DMS) in the presence of a base (typically NaOH). Chitosan is insoluble in aqueous solutions under such basic conditions so the reaction will typically be performed in highly polar organic solvent such as N-methyl-2-pyrrolidone (NMP). Previous investigation has shown that that methylation of chitosan with MeI as methylating reagent and NaOH as base will result only in partial N,N,N-trimethylation and high degree of O-methylation (A. B. Sieval, et al., Carbohyd. Polym., 36 (1998) 157-165). Some approaches have been reported to produce trimethylchitosan with degree of N,N,N-trimethylation accompanied and minimal O-methylation. Runarsson et al. have reported methylation with MeI as methylating agent and 1:1 Dimethyl formamide (DMF):Water ($H_2O$) as solvent and NaOH as base (Ö. V. Runarsson et al., Carbohyd. Polym., 74 (2008) 740-744). The reaction time was 4×48 h with large excess of methylating agent for each 48 h reaction with precipitation and re-dissolving the intermediate product after each addition. With this method 86% N, N, N-trimethylation was obtained with very low O-methylation. Another reported method is reductive alkylation (N, N-dimethylation) in the first step and methylation with a MeI. This two-step procedure resulted in 73% N, N, N-trimethylation with low O-methylation (Verheul, R. J., et al. Biomaterials 29 (2008) 3642-3649). Benediktsdóttir et al. have reported synthesis of N, N, N-trimethylchitosan from TBDMS chitosan (B. E. Benediktsdóttir et al., Carbohyd. Polym., 86 (2011) 1451-1460). In this procedure the chitosan hydroxyl groups are protected by reaction TBDMSCI. The purified intermediate is then N-methylated with MeI, using NMP as solvent and $Cs_2CO_3$ as base. The intermediate is isolated and then deprotection with 1 M TBAF in NMP (72 h reaction) to obtain trimethylchitosan with 100% N, N, N-trimethylation and very low 0 methylation. This procedure is can be used to achieve the goal of very high N, N, N-trimethylation and very low O-methylation but it requires three steps and expensive reagents and is therefore not suitable for large scale production.

SUMMARY

The present invention provides a simple and efficient procedure for the synthesizing trialkylated chitosan, e.g. trimethylchitosan, with very high degree of N,N,N-trialkylation and very low O-alkylation. The procedure is based on dissolving the reagent chitosan in acid and the use of a base and a moderate excess of the alkylating agent in a polar water-miscible solvent to yield the desired N,N,N-trialkylated compound in a single alkylation step. No isolation or purification of an intermediate, partially N-alkylated or N,N-dialkylated compound is required. Furthermore the same approach can be used for to prepare N-alkylated chitosan derivatives with mixed alkylation by using more than one alkylation agent.

The invention in an aspect relates to a method of the preparation of N-alkylated chitosan the method comprising steps of (a) dissolving chitosan, preferably in an acidic solution;

(b) adding at least one suitable alkylation agent and at least one base in a water-miscible organic solvent, to obtain N,N,N-trialkylated chitosan in a single alkylation step (b).

In another aspect, the invention relates to a method for the preparation of a compound of Formula (1)

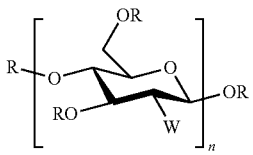

(I)

wherein
n is an integer greater than or equal to 3,
W is N-acetyl:

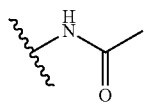

in from 0 to 70 molar % of monomer units (glucosamine units),
and when it is not N-acetyl it is a group selected from:

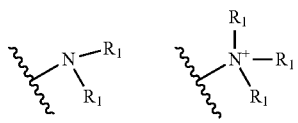

wherein each $R_1$ substituent may be the same or different and is independently selected from H, $CH_3$, and $-(CH_2)_a-CH_3$, wherein a is from 1 to 11, or
when W is not N-acetyl it is a group selected from:

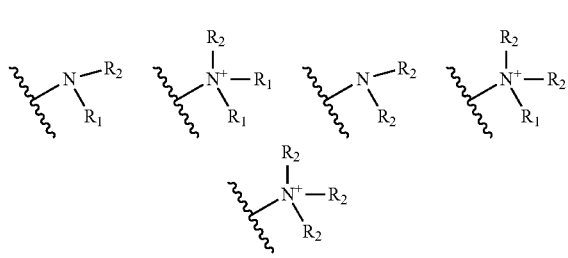

wherein each $R_1$ substituent is independently selected from H, $CH_3$, and $-(CH_2)_a-CH_3$,
wherein a is from 1 to 11, and wherein $R_2$ is selected from:

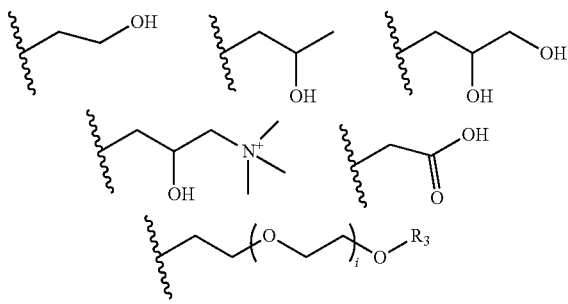

wherein i is an integer from 1-200, preferably 1-50, more preferably 1-10, and $R_3$ is selected from H, $-(CH_2)_j-CH_3$ and $-CO-(CH_2)_j-CH_3$, wherein j is 0, 1, 2, 3, 4 or 5; and wherein R is H in at least 75 molar % of the total number of positions, and when it is not H, R is the same as either amino substituent $R_1$ or $R_2$ on substituent W;
or a salt thereof,
the method comprising steps of
(a) dissolving a chitosan compound with formula

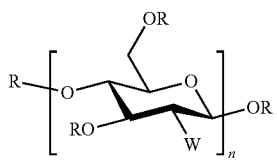

wherein n is an integer greater than or equal to 3, wherein R is H and wherein W is $-NH_2$ or N-acetyl,
or a salt thereof, in a solution that contains at least 1 equivalent of an acid for each equivalent of $-NH_2$ in the chitosan compound;
(b) adding at least one alkylation agent selected from:
(i) alkyl halides, dialkyl sulfates, dialkyl, alkyl methanosulfonates, carbonates, and alkyl-p-toluenesulfontes, with structure:

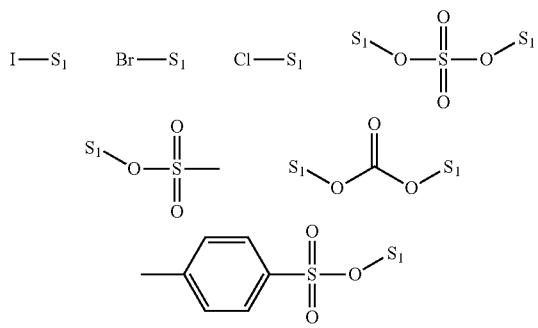

wherein each $S_1$ substituent is independently selected from $CH_3$, and $-(CH_2)_a-CH_3$,
wherein a is from 1 to 11, or wherein $S_1$ is selected from:

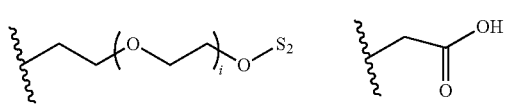

wherein i is an integer from 1-200, preferably 1-50, more preferably 1-10, and $S_2$ is selected from H, $-(CH_2)_j-CH_3$ and $-CO-(CH_2)_j-CH_3$, wherein j is 0, 1, 2, 3, 4 or 5
and (ii) alkyl epoxides selected from:

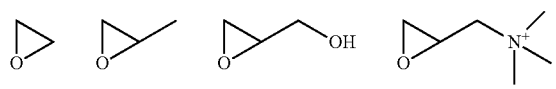

and at least one base, in an amount that is at least sufficient to neutralize the acid of step (a).
Thereby the method results in formation of the desired N,N,N-trialkylated compound in a single alkylation step.
In some embodiments chitosan dry salt is initially prepared by dissolving chitosan in an acidic solution and then precipitating the chitosan as a salt. The chitosan can then be dissolved in water in the salt form without further addition of acid.

The base and alkylating agent can be added in any order or concomitantly. Accordingly, in some embodiments, the alkylating agent is added prior to adding the base. In some embodiments, the base is added prior to adding the alkylating agent. In some embodiments, the base and the alkylating agent are added concomitantly.

If desired, the reaction to prepare N-alkylated chitosan derivatives can be repeated to obtain very high degree of trialkylation with minimal O-alkylation. Accordingly, in certain embodiments, the product N-alkylated chitosan is subjected to a second round of N-alkylation using the same reagents as in the first round of alkylation. Thus the method of the invention can further comprise isolating the product N-alkylated compound of formula (1) and subjecting the thus isolated product to a second round of treatment according to step (b), wherein in the second round of treatment, the same or different alkylation reagent is used, compared with the alkylation reagent used to isolate the isolated N-alkylated compound. As a result of the second round of treatment, a further product N-alkylated compound of formula (1) with a higher degree of N,N,N-trialkylation is obtained.

Preferably, the intermediate compound (the product of the first alkylation reaction) is dissolved prior to performing the second alkylating step. The dissolving can involve the addition of acid.

The invention also relates to N-alkylated chitosan compounds. Thus, in another aspect the invention relates to compounds having the formula

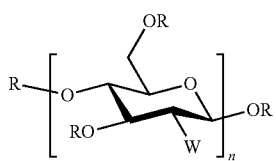

(I)

wherein
n is an integer greater than or equal to 3,
wherein W is N-acetyl:

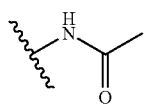

in from 0 to 70 molar % of monomer units and when W is not N-acetyl it is a group selected from:

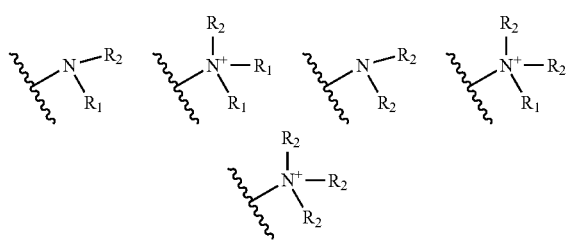

wherein each $R_1$ substituent may independently be selected from H, $CH_3$, and —$(CH_2)_a$—$CH_3$, wherein a is from 1 to 11, and wherein $R_2$ may be selected from:

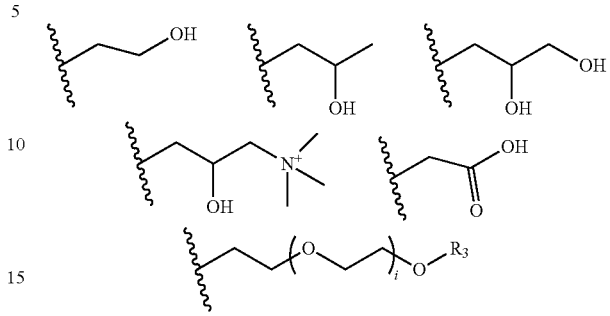

wherein i is an integer from 1-200, preferably 1-50, more preferably 1-10, and $R_3$ is selected from H, —$(CH_2)_j$—$CH_3$ and —CO—$(CH_2)_j$—$CH_3$, wherein j is 0, 1, 2, 3, 4 or 5, wherein R is H in at least 75% of the total number of positions, and when it is not H, R is the same as amino substituent $R_1$ or $R_2$ in W;
or a salt thereof.

When trisubstituted, the N,N,N-alkylated compound can be a salt having any suitable counterion. In some embodiments, the N,N,N-alkylated compound is a salt that has a counterion that is selected from $Cl^-$, $Br^-$ and $CH_3OSO_2O^-$.

In some embodiments, $R_1$ is not H in all monomer units, i.e., not all of the monomer units contain H in the $R_1$ position. In some embodiments, $R_1$ is not H in at least 5% of monomer units, in at least 10% of monomer units or at least 20% of monomer units.

The compounds described herein can be used in treatment options known for chitosan, including their use as bacteriocidal agents, as fungicidal agents, as mucoadhesives, as haemostatic agents, as tissue regeneration agents, as wound healing agent or as bone regeneration agents.

The above features along with additional details of the invention, are described further in the below description and examples, which are intended to further illustrate the invention but are not intended to limit its scope in any way.

BRIEF DESCRIPTION OF THE DRAWINGS

The skilled person will understand that the drawings, described below, are for illustration purposes only. The drawings are not intended to limit the scope of the present teachings in any way.

DESCRIPTION

Figure 1:
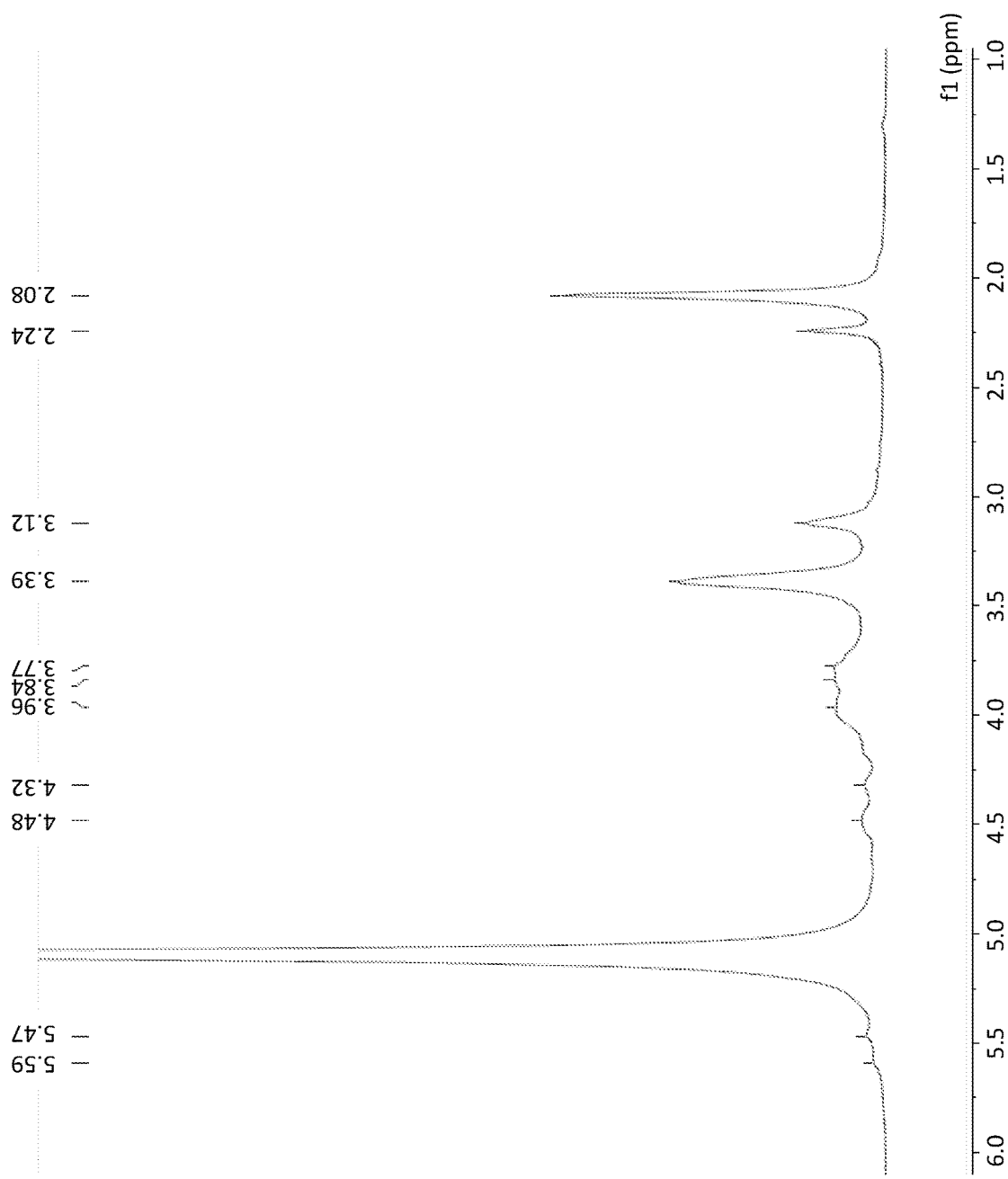
FIG. 1 shows $H^1$-NMR spectrum of the product from Example 1—the solvent was $D_2O$+acetic acid-$d_4$

In the following, exemplary embodiments of the invention will be described, referring to the figures. These examples are provided to provide further understanding of the invention, without limiting its scope.

In the following description, a series of steps are described. The skilled person will appreciate that unless required by the context, the order of steps is not critical for the resulting configuration and its effect. Further, it will be apparent to the skilled person that irrespective of the order of steps, the presence or absence of time delay between steps, can be present between some or all of the described steps.

The invention relates to novel N-alkylated chitosan derivatives, as well as a method for preparing such N-substituted chitosan derivatives. The procedure in general can be carried out only a relatively small excess of the alkylating agent, much less excess than in the original procedure disclosed for the preparation of N-methylated chitosan (700% excess of methylating agent). The process of preparing N-alkylated chitosan can also be carried out in a single alkylation step, not requiring the isolation of intermediate compounds. This is a distinct advantage over prior art methods of preparing e.g. trimethylchitosan, which require the isolation of intermediate dimethylchitosan.

Moreover, the resulting compound can be produced with minimal O-alkylation, which is a major side product in the preparation of trimethylchitosan.

Chitosan is the deacetylated form of chitin. When fully deacetylated, chitosan is a polymer of 2-amino-2-deoxy-D-glucose linked by β-(1-4) bonds. When partically (i.e., not 100%) deacetylated, chitosan is a copolymer of N-acetyl-2-amino-2-deoxygl-D-glucose and 2-amino-2-deoxy-D-glucose. Chitosan is normally obtained by deacetylation of chitin. However, since it is difficult to obtain fully deacetylated chitin, chitosan normally contains some N-acetylation. As a consequence, the method and compounds described herein can contain a portion of N-acetylated material; in other words, the chitosan as described herein can be either completely or partially deacetylated. However, the acetylated portion of the starting material will not react with the methylation agents described herein and will therefore remain silent in the synthetic process of the N-substituted chitosan derivatives.

Chitosan has versatile applications, such as in medicine, food agriculture, cosmetics, nutraceutical, environment friendly packaging and others.

Chitosan has been postulated to be useful in the treatment of a number of human conditions. The compound is useful in medical treatment since it has high degree of biocompatibility and is biodegradable. Chitosan has bacteriocidal activity and is well adsorbed. As a consequence, chitosan is useful in wound treatment and can be used in e.q. wound dressings and to dampen immunologic mediators such as IL-8, prostaglandin E, IL-1 beta and others. Chitosan can be formulated using known methods, e.g., as beads, gels, microparticles, nanoparticles, nanofibers and as scaffold to support normal (healthy) tissue. Chitosan is thus used in 3D scaffolds such as gels and sponges.

In addition to its bacteriocidal activity, haemostatic activity and antifungal activity chitosan can be used in chitosan sponges (a type of porous dressing) that have exudative properties in wound treatment in addition as aiding in tissue regeneration, including bone regeneration, thus promoting bone regeneration. Chitosan has a range of other uses, such as in waste water treatment, in heavy metal removal, as focculating agent, as an antioxidant and for skin protection in cosmetic compositions. The compounds described herein are contemplated to be useful in all known uses of chitosan, including but not limited to the foregoing.

Despite its large range of useful properties, chitosan possesses poor aqueous solubility, which gives rise to different chemical modifications of chitosan in order to obtain better water solubility and improve biological properties. Two of the most notable derivatives are N,N,N-trimethyl chitosan (TMC) and carboxymethyl chitosan (CMC). TMC is soluble in aqueous solutions and it has shown that this chitosan derivative can be remarkably more active against bacterial infections than unmodified chitosan and may also have significant value as an absorption enhancer for drug delivery applications (Benediktsdóttir et al. 2014).

N,N,N-trimethylchitosan (TMC) is produced by N-methylation of chitosan. Typically alkylating reagents like methyl iodide (MeI) have been used for this purpose. The resulting product possesses a permanent positive charge and improved aqueous solubility in a wide pH range compared to native chitosan (Benediktsdóttir et al. 2014). With these improved properties, TMC is a good candidate for a variety of uses, including in drug delivery systems and gene delivery at physiological pH, as an antibacterial compound or in the treatment in various human conditions. However, traditional protocols that use MeI as methylating reagent and NaOH as base will result only in partial N,N,N-trimethylation and high degree of O-methylation. This is a great disadvantage, in particular for scale-up, since synthetic protocols therefore must include additional reaction steps and/or purification steps.

The present invention makes it feasible to prepare N,N,N-trimethylchitosan in high yield with minimal O-methylation, thereby providing a distinct advantage over prior art protocols. The invention also relates to a novel method of preparing alkylated chitosan, The invention further provides novel N-alkylated chitosan derivatives. These derivatives can be used in methods and processes known for chitosan, for example as antibacterial, antifungal or antiviral agents, in haemostasis, in drug delivery systems and gene delivery, in the treatment of human conditions, tissue and bone regeneration, in wound dressings, and as wound-healing agents. The compounds disclosed herein can also be used to enhance drug adsorption.

One advantage of the N-alkylated chitosan derivatives described herein is that the derivatives are in general water soluble and therefore particularly useful in a range of applications. Thus, the insolubility of chitosan is overcome by the N-alkylation, while retaining the beneficial characteristics of the chitosan compound.

During the reaction, the reagents remain largely in solution, despite the fact that chitosan should be (thermodynamically) insoluble under basic or neutral conditions. A key feature of the method is the prior dissolution of the chitosan by the addition of acid (thereby forming a chitosan salt) before adding the alkylating agent(s). During the subsequent reaction with alkylating agent(s), the reagents and product remain largely in solution. For this purpose, it can be beneficial to add the base slowly to the reaction mixture, so as to slowly raise the pH of the solution and thereby prevent the precipitation of reagents in the solution as the pH is raised. The alkylation proceeds in a single reaction; isolation of intermediate partially alkylated compounds is not required or needed.

Chitosan is a deacetylated form of chitin. In general, chitosan is partially deacetylated, which means that the chitosan is a heterogeneous mixture of oligomers containing different amount of N-acetylation. Overall, the chitosan compound used as reagent in the present invention can be from 1 to 60% N-acetylated, such as from 1 to 50% N-acetylated, from 1 to 40% N-acetylated, from 1 to 30%

N-acetylated, from 1 to 20% N-acetylated, or from 1 to 10% N-acetylated (all percentages being molar %).

The inventors have found that by treatment with acid prior to the addition of alkylating agent, the reagents are brought into solution, thereby increasing the yield of the subsequent alkylation step.

The acid can be any mineral acid, such as hydrochloric acid, hydrobromic acid, hydrofluoric acid, perchloric acid, nitric acid, or mixtures of such acids. Preferably the mineral acid is a monovalent acid.

The acid can also be one or more organic acid, such as acetic acid, formic acid, oxalic acid, lactic acid, propionic acid, maleic acid, succinic acid, methanesulfonic, acid, p-toluenesulfonic acid.

Preferably, there should be at least one equivalent of acid added for each equivalent of $NH_2$ in the reactant chitosan compound. If an excess of acid is used, i.e. more than one equivalent per $NH_2$ group, an increased amount of base is required in the subsequent step.

An alkylating agent and at least one base is subsequently added to the aqueous chitosan solution. The alkylating agent and base can be added concomitantly or in any order. The alkylating agent can be added prior to the base. There should be at least enough base added to neutralize the acid that was added to the reaction mixture. In some embodiments, there is from 1 to 20 equivalents added, relative to the equivalents of amino groups, from 1 to 15 equivalents, from 1 to 10 equivalents, from 1 to 5 equivalents, from 1 to 4 equivalents, from 1 to 3 equivalents or from 1 to 2 equivalents.

The amount of base can further be from 0 to 5 equivalents relative to the number of equivalents of alkylating agents in the reaction, such as from 0 to 4 equivalents, from 0 to 3 equivalents, from 0 to 2 equivalents, or from 1 to 2 equivalents.

The base can in principle be any base, such as for example sodium hydroxide. It can however be beneficial to use a mild or weak base. Useful bases in the reaction can for example be one or more of $NaHCO_3$, $Na_2CO_3$, $KHCO_3$, $K_2CO_3$, $RbHCO_3$, $Rb_2CO_3$, $CsHCO_3$, $Cs_2CO_3$, triethylamine, tripropylamine, tributylamine, triisopropylamine, triisobutylamine, N,N,-diisobutylmethylamine, triisopropanolamine, N,N-diisopropylethylamine, N,N,-diisopropyl aniline, 1,8-Diazabicyclo(5.4.0)undec-7-ene (DBU). Other weak bases known in the art are however also contemplated. A single base can be added, or a mixture of bases (e.g. a mixture of $NaHCO_3$ and $Na_2CO_3$).

The procedure in general can be carried out only a relatively small excess of the alkylating agent. Thus, in general the alkylating agent is added in a stoichiometry that is at least 1:1 with respect to the equivalents of $NH_2$ in the starting chitosan compound. In some embodiments, the alkylating agent in an amount of from 1 to 15 equivalents, from 1 to 12 equivalents, from 1 to 10 equivalents, from 1 to 9 equivalents, from 1 to 8 equivalents, from 1 to 6 equivalents, from 1 to 4 equivalents, or from 1 to 3 equivalents with respect to the equivalents of $NH_2$ in the starting chitosan compound.

An advantage of using a relatively low excess of alkylating agent is that the degree of O-alkylation can be kept to a minimum in the reaction. In general, the N-alkylated chitosan product of the reaction can have less than about 25% O-alkylation, less than about 20% O-alkylation, less than about 15% O-alkylation, less than about 10% O-alkylation, less than about 5% O-alkylation, less than about 2% O-alkylation, or less than about 1% O-alkylation (all being molar %). In an embodiment, the reaction product is essentially free of O-alkylation. The method of the invention can thus further comprise a step of determining the degree of O-alkylation in the product. The O-alkylation as so determined can therefore preferably be found to be (molar %) less than about 25% O-alkylation, less than about 20% O-alkylation, less than about 15% O-alkylation, less than about 10% O-alkylation, less than about 5% O-alkylation, less than about 2% O-alkylation, or less than about 1% O-alkylation. In some embodiments, the O-alkylation is not detectable.

The method can accordingly include a step of determining the degree of O-alkylation in the product(s), with the O-alkylation as so determined being as described in the foregoing.

During the alkylation reaction, acid that is formed is neutralized by the base. Thereby, the reaction proceeds under alkaline conditions despite the formation of acid.

The solvent used in the method can comprise at least one water-miscible solvent. The solvent can be in a mixture with water. Thus, in some embodiments, the starting material is dissolved in a a water-miscible solvent, such as a water miscible polar solvent, or a mixture of two or more such water miscible polar solvents. Exemplary solvents that are useful include N,N-Dimethylformamide (DMF), N-Methyl-2-pyrrolidone (NMP), dimethyl sulfoxide (DMSO), NMP and DMSO N, N-dimethylacetamide (DMAC), 1,4-dioxane, methanol, ethanol, tetrahydrofuran, acetonitrile. The solvent can include any one of these solvents, or mixtures of two or more of these solvents, optionally in a mixture with water.

Although it may be useful to carry out the reaction at relatively low temperature, the alkylation reaction can in general be carried out at any suitable temperature. The reaction can be carried out at a temperature that is preferably at least 20° C. It can be useful to carry out the reaction at higher temperatures, such as at least 30° C., at least 40° C., at least 50° C., at least 60° C., at least 80° C., at least 100° C., or at least 120° C. Temperatures above the boiling point of the solvent can be achieved by carrying out the reaction under pressure.

In some embodiments, the temperature of the reaction is in the range of 20° C. to 200° C., in the range of 20° C. to 150° C., in the range of 20° C. to 100° C., in the range of 40° C. to 70° C., or in the range of 50° C. to 60° C.

Although not required, it can be beneficial to carry out the alkylation reaction in the presence of a catalyst. Useful catalysts known in the art include sodium iodide.

It can be useful to repeat the reaction to achieve an increased amount of N,N,N-trialkylation. Thus, the product alkylated material can be isolated from the reaction and subjected to a repeated reaction with alkylating agent. The alkylating agent in this second alkylation reaction can be the same as in the first reaction, so as maximize the degree of trialkylation. For example, in the preparation of trimethylated chitosan (TMC), the reaction with methyl iodide can be repeated so as to maximize the yield of trimethylated chitosan, and minimize the amount of dimethylated compound. The product compound from the first reaction in such repeated alkylation is preferably dissolved, for example by treatment with acid, prior to the second round of treatment with alkylating agent.

The alkylating reagent in the second alkylation can also be different from the alkylating agent used in the first alkylation reaction. This has the advantage of being able to tailor the product obtained, both in terms of composition of the alkylating groups and also in terms of the degree of N-substitution with particular groups. For example, in the preparation of a compound that contains a high degree of N-methylation and a smaller degree of alkylation with a longer alkyl group (for example propyl or butyl), it can be advantageous to carry out the first reaction in the presence of a less reactive alkylation reagent (such as a halide with long alkyl chain) only, to be followed by a second reaction with a reaction with more reactive agent (such as methyl iodide), so as to introduce the desired amount of alkylation with two (or more) different alkyl groups in the final product. The alkylation can be carried out in this manner using any combination of alkyl groups, varying the reaction conditions (such as amount of alkylating reagent) to achieve the degree and composition of N-alkylation that is desired.

One advantage of the reaction conditions described herein is that O-alkylation, a major side reaction of N-alkylation reactions of chitosan, is very low. In general the amount of O-alkylation is less than about 25% O-alkylation (referring to all O groups in the chitosan reactant), preferably less than about 20%, more preferably less than about 15%, more preferably less than about 10%, even more preferably less than about 5%, even more preferably less than about 2%, most preferably less than about 1% (all being molar %).

The alkylated chitosan derivatives disclosed herein can be useful for use as a medicament. When formulated for pharmaceutical use, e.g. as medicaments or in medical protocols or medical treatments, the alkylated chitosan derivatives disclosed herein, including for example trimethylchitosan, can be formulated using known formulation methods, including formulations as beads, gels, microparticles, nanoparticles, nanofibers and as tissue-supporting scaffolds. For example, the chitosan derivatives can be used as bacteriocidal agents, as fungicidal agents, as mucoadhesives, as haemostatic agents, as tissue regeneration agents, as wound healing agent or as bone regeneration agents.

The alkylated chitosan derivatives may also be formulated as tablets or capsules. The formulations can be adapted for non-invasive or invasive delivery. For example the compositions may be formulated for oral, topical, transmucosal, vaginal, ocular and rectal or inhalation delivery. The compositions may also, or alternatively, be formulated for injection. The compositions may further be formulated for immediate or sustained delivery, or the compositions may be formulated for delayed delivery.

The formulations may include one or more pharmaceutically acceptable excipient. Such excipients generally can serve the role of providing the resulting composition with increased long-term stability, facilitate adsorption, enhance solubility, providing flowability or non-stick properties and also prevent degradation or aggregation over time.

Exemplary excipients include fillers, binders, disintegrants, coatings, sorbents, antiadherents, lubricants, glidants, preservatives, antioxidants, flavouring agents, sweeteners, colouring agents, solvents, buffering agents, chelating agents, viscosity imparting agents, surface active agents and humectants.

The novel N-alkylated compounds can also be used as excipients in pharmaceutical formulations (see Singh et al., Int J Pharm Sci Res 2 (2011) 2266-2277). As should be apparent from the foregoing, some of the advantage of the present invention include:
1. Novel N-alkylated chitosan derivatives that are water soluble and therefore particularly useful in a range of applications.
2. A one-pot synthetic process of N-alkylated chitosan, including trimethylchitosan, not requiring the isolation of intermediate compounds.
3. Minimal O-alkylation in the resulting product compound.
4. Use of a small excess of the alkylation agent, thus resulting in reduced cost of synthesis 5. Relatively short reaction time (hours not many days)
6. Synthetic protocol that is easily scalable for industrial production.
7. The reaction can be repeated to obtain very high degree of trialkylation with minimal O-alkylation.
8. Alkylation can be directed by repeating alkylation reaction and/or using a mixture of alkylating agents.

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

Throughout the description and claims, the terms "comprise", "including", "having", and "contain" and their variations should be understood as meaning "including but not limited to", and are not intended to exclude other components.

The present invention also covers the exact terms, features, values and ranges etc. in case these terms, features, values and ranges etc. are used in conjunction with terms such as about, around, generally, substantially, essentially, at least etc. (i.e., "about 3" shall also cover exactly 3 or "substantially constant" shall also cover exactly constant).

The term "at least one" should be understood as meaning "one or more", and therefore includes both embodiments that include one or multiple components. Furthermore, dependent claims that refer to independent claims that describe features with "at least one" have the same meaning, both when the feature is referred to as "the" and "the at least one".

It will be appreciated that variations to the foregoing embodiments of the invention can be made while still falling within the scope of the invention can be made while still falling within scope of the invention. Features disclosed in the specification, unless stated otherwise, can be replaced by alternative features serving the same, equivalent or similar purpose. Thus, unless stated otherwise, each feature disclosed represents one example of a generic series of equivalent or similar features.

Use of exemplary language, such as "for instance", "such as", "for example" and the like, is merely intended to better illustrate the invention and does not indicate a limitation on the scope of the invention unless so claimed. Any steps described in the specification may be performed in any order or simultaneously, unless the context clearly indicates otherwise.

All of the features and/or steps disclosed in the specification can be combined in any combination, except for combinations where at least some of the features and/or steps are mutually exclusive. In particular, preferred features of the invention are applicable to all aspects of the invention and may be used in any combination.

EXAMPLES

In the following, non-limiting experimental examples in accordance with the invention are described.

Example 1

In a two-necked round bottom flask, 1 g chitosan (DA=17.8%) 40 mL DMF:$H_2O$ [1:1] and 1.5 eq. HCl is added and stirred at room temperature overnight to fully dissolve the chitosan. (1 g of this chitosan was calculated to contain 6 mmol of monomer units. 1 equivalent (eq.) is thus equal to 6 mmol. 1 equivalent (eq.) in this and subsequent examples is thus equal to 6 mmol). Then 6 eq. methyl iodide is added drop wise. After stirring for one hour at room temperature, the reaction mixture is refluxed at 60° C. followed by the drop wise addition of 2 eq. sodium bicarbonate in a 1M solution in H$_2$O with the help of an addition funnel. After 6 hours reaction 2 eq. sodium bicarbonate is added again with vigorous stirring. After 20 hours of heating and refluxing the reaction mixture, it is allowed to room temperature, the product is precipitated with 200 mL EtOH, and then filtered on sintered funnel. The solid is washed with excess of acetone and allowed to air dry overnight. Dialyzed against 10% NaCl solution for 3 days, followed by dialysis against pure water for 4 days. Freeze-dried to obtain the product.

The degree of N,N,N-trimethylation (D-TM) of the free amino groups in the N-methylated chitosan product was 72% and N,N-dimethylation (D-DM) was 28% according to H$^1$-NMR (FIG. 1) and O-methylation was not detected.

Example 2

In a two-necked round bottom flask, 1 g chitosan, 40 mL DMF:H$_2$O [1:1] and 2 eq. HCl is added and stirred at room temperature overnight to fully dissolve the chitosan. Then 6 eq. methyl iodide is added drop wise. After stirring for one hour at room temperature, the reaction mixture is refluxed at 60° C. followed by the drop wise addition of 2 eq. sodium bicarbonate in a 1M solution in H$_2$O with the help of an addition funnel. After 6 hours reaction 2 eq. sodium bicarbonate is added again with vigorous stirring. After 20 hours of heating and refluxing the reaction mixture, it is allowed to room temperature, the product is precipitated with 300 mL EtOH, and then filtered on sintered funnel. The solid is washed with excess of acetone and allowed to air dry overnight. Dialyzed against 10% NaCl solution for 3 days, followed by dialysis against pure water for 4 days. Freeze-dried to obtain the product.

Figure 2:
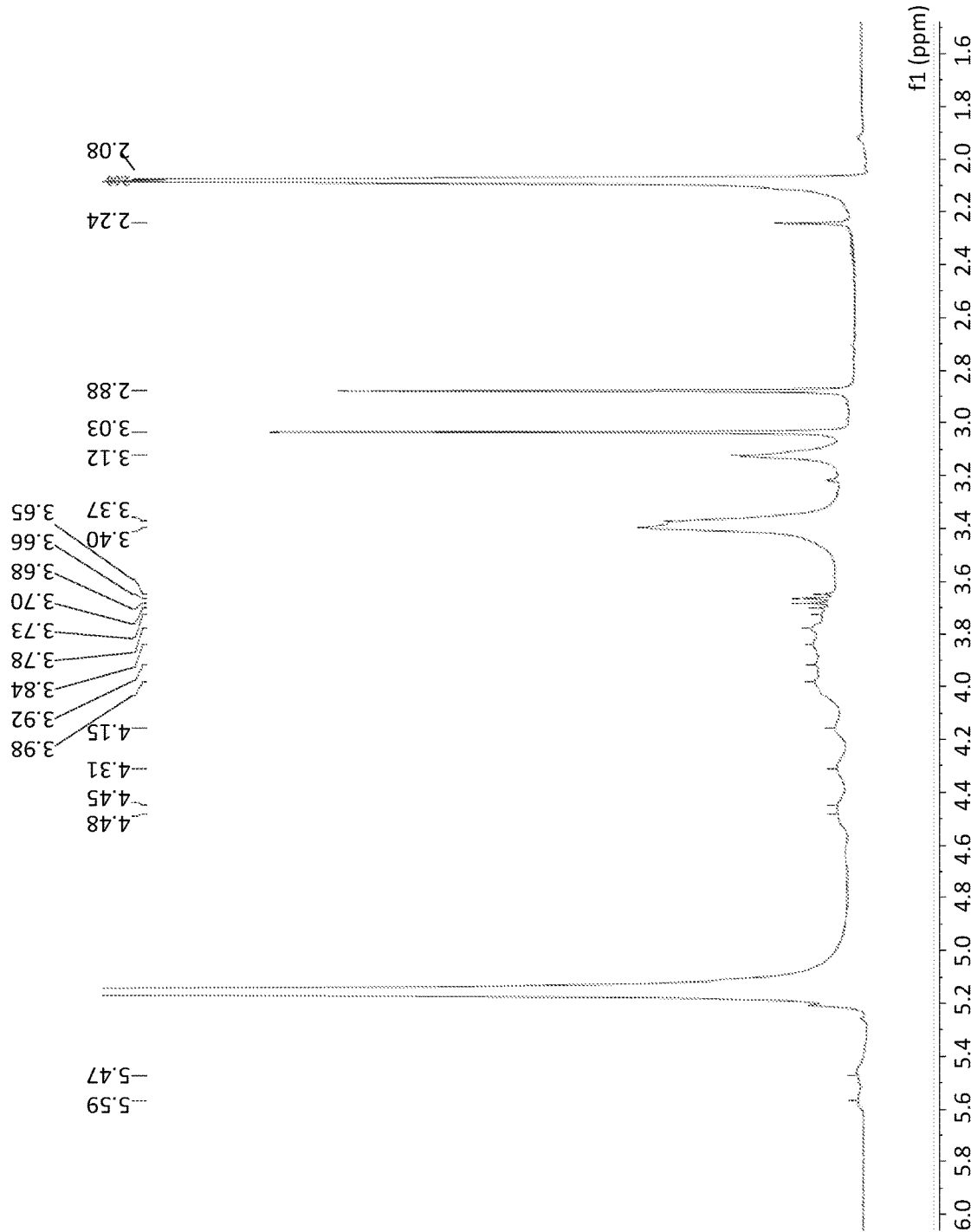
FIG. 2 shows $H^1$-NMR spectrum of product from Example 2—the solvent is $D_2O$+acetic acid-$d_4$

The degree of N,N,N-trimethylation (D-TM) in the N-methylated chitosan product was 68% and N,N-dimethylation (D-DM) was 32% according to H$^1$-NMR (FIG. 2) and O-methylation was not detected.

Example 3

Figure 3:
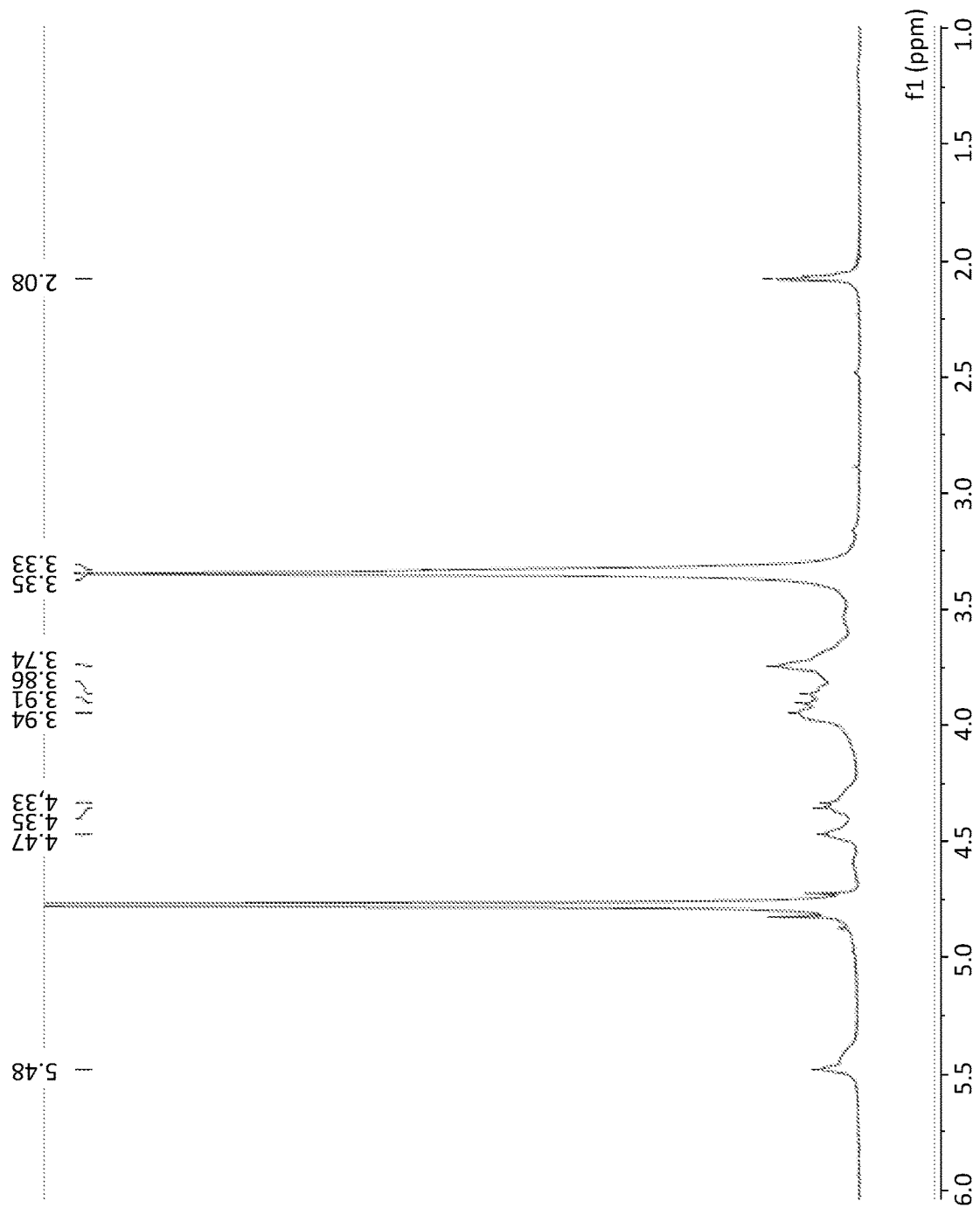
FIG. 3 shows $H^1$-NMR spectrum of product from Example 3—the solvent is $D_2O$+acetic acid-$d_4$. Dialyzed sample of the material.

The reaction scheme as detailed in Example 1 was repeated, with the difference that after the precipitation step the reaction was repeated, resulting in this case an N,N,N-trimethylation (D-TM) yield of 99% in the N-methylated chitosan product with N,N-dimethylation (D-DM) about 1% according to H$^1$-NMR (FIG. 3) and O-methylation was minimal (less than 10%).

Example 4. N-methylation

In a two-necked round bottom flask, 1 g chitosan, 40 mL DMSO:H$_2$O [1:1] and 1 eq. HCl is added and stirred at room temperature overnight to fully dissolve the chitosan. Then 6 eq. methyl iodide is added dropwise. After stirring for one hour at room temperature, the reaction mixture is refluxed at 60° C. followed by the drop wise addition of 2 eq. sodium bicarbonate in a 1M solution in H$_2$O with the help of an addition funnel. After 24 hours reaction 2 eq. sodium bicarbonate is added again with vigorous stirring. After 48 hours of heating and refluxing the reaction mixture, it is allowed to room temperature, the product is precipitated with 300 mL EtOH, and then filtered on sintered funnel. The solid is washed with excess of acetone and allowed to air dry overnight. Dialyzed against 10% NaCl solution for 3 days, followed by dialysis against pure water for 4 days. Freeze-dried to obtain the product.

Figure 4:
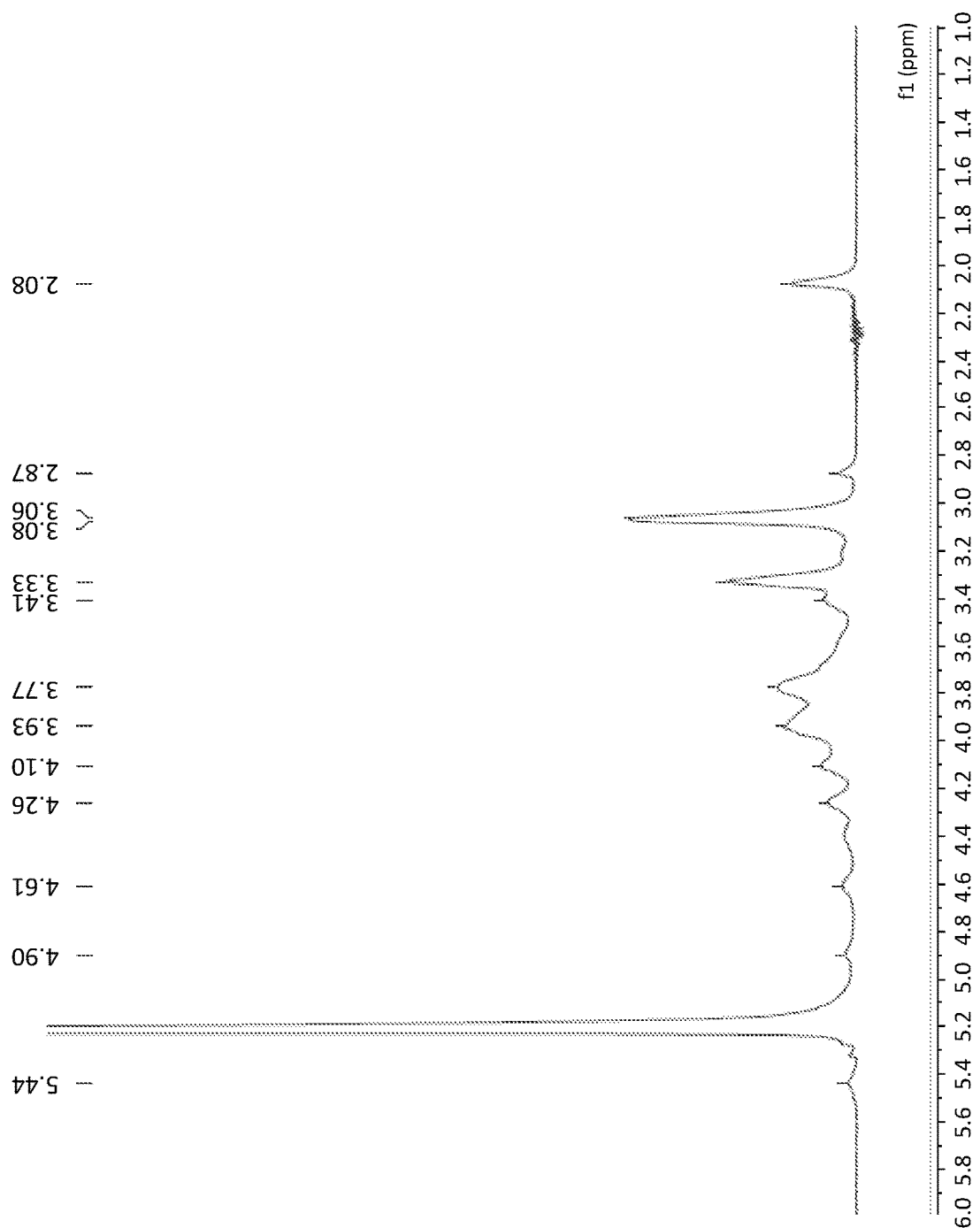
FIG. 4 shows $H_1$-NMR spectrum of product from Example 4—the solvent is $D_2O$. Dialyzed sample of the material.

The degree of N,N,N-trimethylation (D-TM) in the N-methylated chitosan product was 26% and N,N-dimethylation (D-DM) was 67% and N-monomethylation (D-MM) was 1% according to H$^1$-NMR (FIG. 4) and O-methylation was not detected.

Example 5. N-ethylation (N-alkylation)

In a two-necked round bottom flask, 1 g chitosan, 40 mL DMF:H$_2$O [1:1] and 1.5 eq. HCl is added and stirred at room temperature overnight to fully dissolve the chitosan. Then 6 eq. ethyl iodide is added drop wise. After stirring for one hour at room temperature, the reaction mixture is refluxed at 60° C. followed by the drop wise addition of 2 eq. sodium bicarbonate in a 1M solution in H$_2$O with the help of an addition funnel. After 6 hours reaction 2 eq. sodium bicarbonate was added again with vigorous stirring. After 20 hours of heating and refluxing the reaction mixture, it is allowed to room temperature, the product is precipitated with 200 mL EtOH, and then filtered on sintered funnel. The solid is washed with excess of acetone and allowed to air dry overnight. Dialyzed against 10% NaCl solution for 3 days, followed by dialysis against pure water for 4 days. Freeze-dried to obtain the product.

Figure 5:
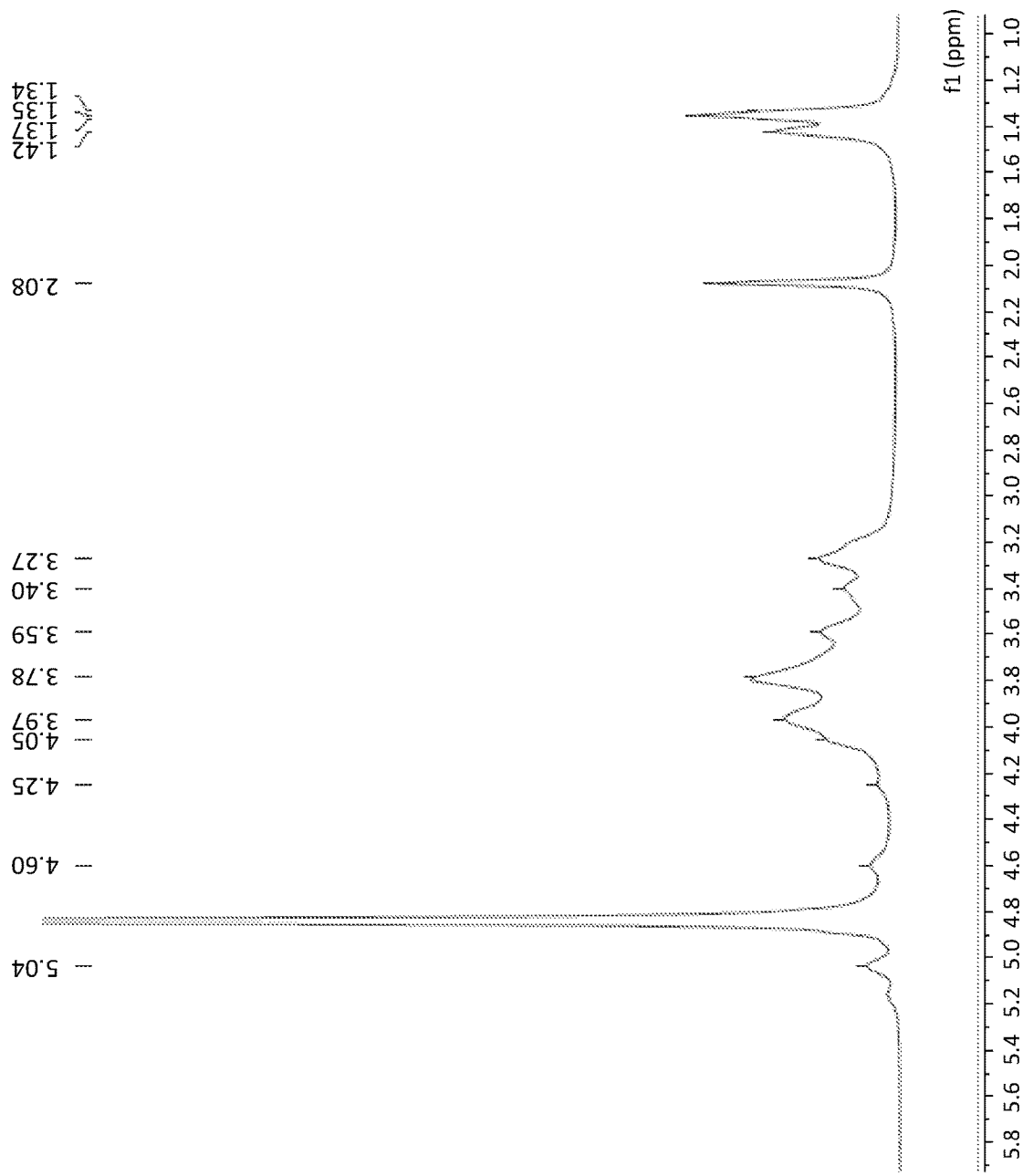
FIG. 5 shows H-NMR spectrum of the product from Example 5. Sample submitted in 1% acetic acid-$d_4$ in $D_2O$.

The degree of N,N,N-trialkylation (D-TA) in the N-ethylated chitosan product was 26% and the N,N-dialkylation (D-DA) was 74% according to H$^1$-NMR (FIG. 5).

Example 6—N-hydroxypropylation and N-methylation

In a two-necked round bottom flask, 1 g chitosan, 40 mL DMF:H$_2$O [1:1] and 1.5 eq. HCl is added and stirred at room temperature overnight to fully dissolve the chitosan. Then 6 eq. propylene oxide) is added followed by the drop wise addition of 2 eq. sodium bicarbonate in a 1M solution in H$_2$O with the help of an addition funnel. After stirring for one hour at room temperature, the reaction mixture is refluxed at 60° C. The reaction mixture is allowed to stir overnight. Next, 6 eq. methyl iodide was added followed by the drop wise addition of 2 eq. sodium bicarbonate in a 1M solution in H$_2$O with the help of an addition funnel. After 6 hours reaction 2 eq. sodium bicarbonate was added again with vigorous stirring. After 20 hours of heating and refluxing the reaction mixture, it is allowed to room temperature, the product is precipitated with 200 mL EtOH, and then filtered on sintered funnel. The solid is washed with excess of acetone and allowed to air dry overnight. Dialyzed against 10% NaCl solution for 3 days, followed by dialysis against pure water for 4 days. Freeze-dried to obtain the product.

Half of the solution is precipitated with cold EtOH and then filtered on sintered funnel. The solid is washed with excess of acetone and is allowed to air-dry overnight resulting in 0.63 g of material. The other half of the solution was ion exchanged and dialyzed without precipitation, followed by freeze-drying, yielding 0.68 g of material.

Figure 6:
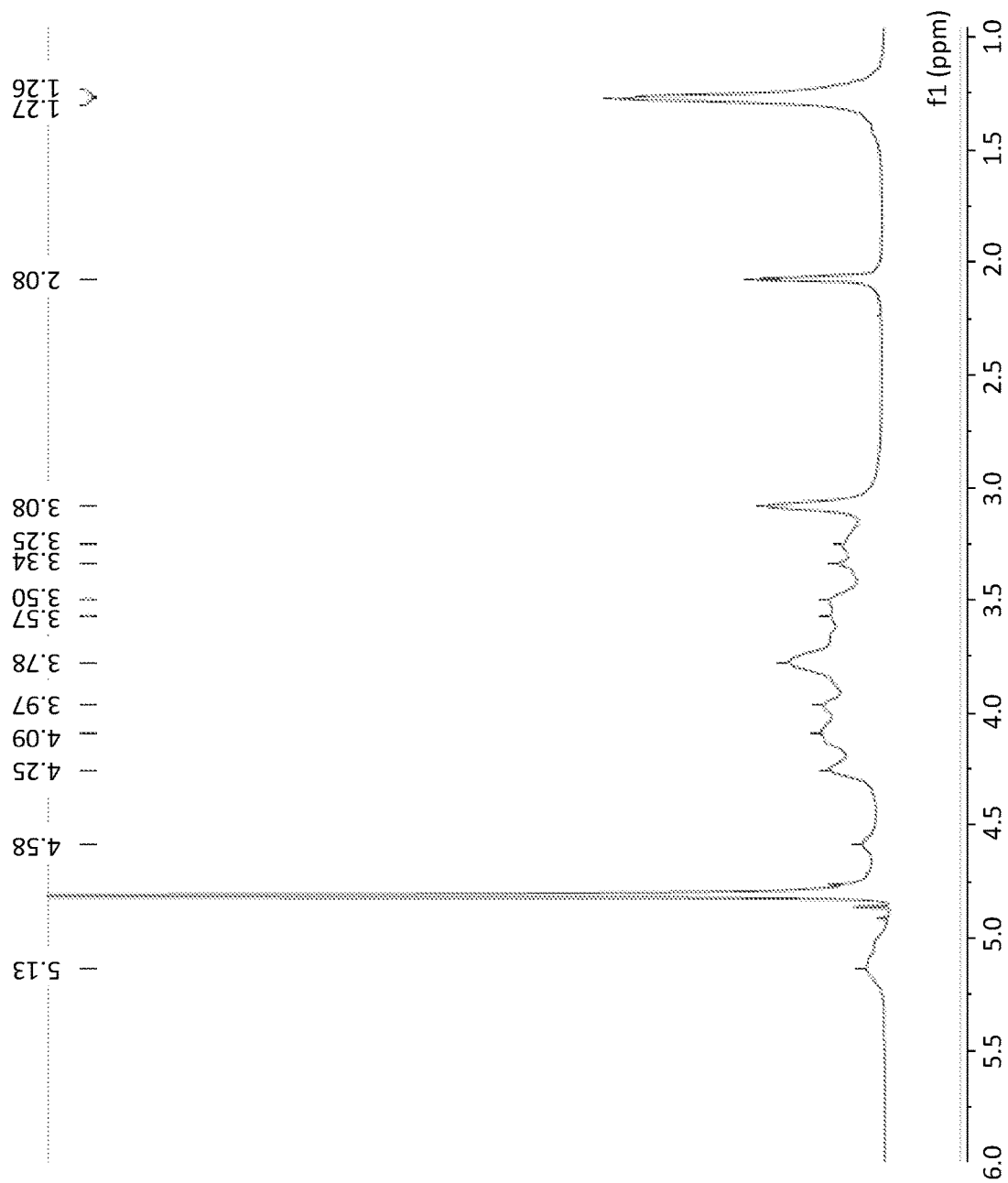
FIG. 6 shows H-NMR spectrum of the product from Example 6. Sample submitted in 1% acetic acid d4 in $D_2O$.

The degree of hydroxypropylation (D-HP) in the chitosan product was 76%, the degree of tetriary methylation (D-TeM) was 35% and the degree of quaternary methylation (D-QM) was 14% according to H$^1$-NMR (FIG. 6).

Example 7

In a two-necked round bottom flask, 1 g chitosan, 40 mL DMF:H$_2$O [1:1] and 1.5 eq. HCl is added and stirred at room temperature overnight to fully dissolve the chitosan. Then 1 eq. propylene oxide is added followed by the drop wise addition of 2 eq. sodium bicarbonate in a 1 M solution in $H_2O$ with the help of an addition funnel. After stirring for one hour at room temperature, the reaction mixture is refluxed at 60° C. The reaction mixture is allowed to stir overnight. Next, 6 eq. methyl iodide was added followed by the drop wise addition of 2 eq. sodium bicarbonate in a 1 M solution in $H_2O$ with the help of an addition funnel. After 6 hours reaction 2 eq. sodium bicarbonate was added again with vigorous stirring. After 20 hours of heating and refluxing the reaction mixture, it is allowed to room temperature, the product is precipitated with 200 mL EtOH, and then filtered on sintered funnel. The solid is washed with excess of acetone and allowed to air dry overnight. Dialyzed against 10% NaCl solution for 3 days, followed by dialysis against pure water for 4 days. Freeze-dried to obtain the product.

The degree of tetriary methylation (D-TeM) was 57% and the degree of quaternary methylation (D-QM) was 37% according to $H^1$-NMR. The degree of hydroxypropylation (D-HP) was 20%.

Example 8

The reaction scheme as detailed in Example 7 was repeated, with the difference that 2 eq. propylene oxide was used.

The degree of tetriary methylation (D-TeM) was 62% and the degree of quaternary methylation (D-QM) was 35% according to $H^1$-NMR. The degree of hydroxypropylation (D-HP) was 14%.

Example 9

The reaction scheme as detailed in Example 7 was repeated, with the difference that 4 eq. propylene oxide was used.

The degree of tetriary methylation (D-TeM) was 49% and the degree of quaternary methylation (D-QM) was 40% according to $H^1$-NMR. The degree of hydroxypropylation (D-HP) was 24%.

Example 10

In a two-necked round bottom flask, 1 g chitosan, 40 mL DMF:$H_2O$ [1:1] and 1.5 eq. HCl is added and stirred at room temperature overnight to fully dissolve the chitosan. Then 3 eq. ethyl iodide is added drop wise. After stirring for one hour at room temperature, the reaction mixture is refluxed at 60° C. followed by the drop wise addition of 2 eq. sodium bicarbonate in a 1M solution in $H_2O$ with the help of an addition funnel. The reaction mixture is allowed to stir overnight. Next, 6 eq. methyl iodide was added followed by the drop wise addition of 2 eq. sodium bicarbonate. After 20 hours of heating and refluxing the reaction mixture, it is allowed to room temperature, the product is precipitated with 200 mL EtOH, and then filtered on sintered funnel. The solid is washed with excess of acetone and allowed to air dry overnight. Dialyzed against 10% NaCl solution for 3 days, followed by dialysis against pure water for 4 days. Freeze-dried to obtain the product.

The degree of N,N,N-trialkylation in the N-ethylated chitosan product was 43% and the N,N-dialkylation was 57% according to $H^1$-NMR. The degree of N-ethylation was 32%.

Example 11

In a two-necked round bottom flask, 1 g chitosan, 40 mL DMSO and 1.5 eq. methanesulfonic acid is added and stirred at room temperature overnight to fully dissolve the chitosan. Then 6 eq. methyl iodide is added drop wise. After stirring for one hour at room temperature, the reaction mixture is refluxed at 60° C. followed by the drop wise addition of 2 eq. N,N-Diisopropylethylamine with the help of a syringe. After 6 hours reaction 2 eq. N,N-Diisopropylethylamine is added again. After 20 hours of heating and refluxing the reaction mixture, it is allowed to room temperature, the product is precipitated with 200 mL EtOH, and then filtered on sintered funnel. The solid is washed with excess of acetone and allowed to air dry overnight. Dialyzed against 10% NaCl solution for 3 days, followed by dialysis against pure water for 4 days. Freeze-dried to obtain the product.

The degree of N,N,N-trimethylation in the N-methylated chitosan product was 60% and N,N-dimethylation was 30% and N-monomethylation was 10% according to $H^1$-NMR and O-methylation was not detected.

Example 12

In a two-necked round bottom flask, 1 g chitosan, 40 mL DMF and 1.5 eq. HCl is added and stirred at room temperature overnight to fully dissolve the chitosan. Then 6 eq. methyl iodide is added drop wise. After stirring for one hour at room temperature, the reaction mixture is refluxed at 60° C. followed by the drop wise addition of 2 eq. N,N-Diisopropylethylamine with the help of a syringe. After 6 hours reaction 2 eq. N,N-Diisopropylethylamine is added again. After 20 hours of heating and refluxing the reaction mixture, it is allowed to room temperature, the product is precipitated with 200 mL EtOH, and then filtered on sintered funnel. The solid is washed with excess of acetone and allowed to air dry overnight. Dialyzed against 10% NaCl solution for 3 days, followed by dialysis against pure water for 4 days. Freeze-dried to obtain the product.

The degree of N,N,N-trimethylation in the N-methylated chitosan product was 67% and N,N-dimethylation was 30% and N-monomethylation was 3% according to $H^1$-NMR and O-methylation was not detected.

Example 13

In a two-necked round bottom flask, 1 g chitosan, 40 mL DMF:$H_2O$ [1:1] and 1.5 eq. HCl is added and stirred at room temperature overnight to fully dissolve the chitosan. Then 6 eq. methyl iodide is added drop wise. After stirring for one hour at room temperature, the reaction mixture is refluxed at 60° C. followed by the drop wise addition of 2 eq. N,N-Diisopropylethylamine with the help of a syringe. After 6 hours reaction 2 eq. N,N-Diisopropylethylamine is added again. After 20 hours of heating and refluxing the reaction mixture, it is allowed to room temperature, the product is precipitated with 200 mL EtOH, and then filtered on sintered funnel. The solid is washed with excess of acetone and allowed to air dry overnight. Dialyzed against 10% NaCl solution for 3 days, followed by dialysis against pure water for 4 days. Freeze-dried to obtain the product.

The degree of N,N,N-trimethylation in the N-methylated chitosan product was 42% and N,N-dimethylation was 56% and N-monomethylation was 5% according to $H^1$-NMR and O-methylation was not detected.

Example 14

In a two-necked round bottom flask, 1 g trimethyl chitosan (obtained by the method described in Example 13), 40 mL DMF:$H_2O$ [1:1] and 1.5 eq. HCl is added and stirred at room temperature overnight to fully dissolve the chitosan. Then 6 eq. methyl iodide is added drop wise. After stirring for one hour at room temperature, the reaction mixture is refluxed at 60° C. followed by the drop wise addition of 2 eq. N,N-Diisopropylethylamine with the help of a syringe. After 6 hours reaction 2 eq. N,N-Diisopropylethylamine is added again. After 20 hours of heating and refluxing the reaction mixture, it is allowed to room temperature, the product is precipitated with 200 mL EtOH, and then filtered on sintered funnel. The solid is washed with excess of acetone and allowed to air dry overnight. Dialyzed against 10% NaCl solution for 3 days, followed by dialysis against pure water for 4 days. Freeze-dried to obtain the product.

The degree of N,N,N-trimethylation in the N-methylated chitosan product was 92% and N,N-dimethylation was 8% according to $H^1$-NMR and O-methylation was not detected.

Example 15

In a two-necked round bottom flask, 1 g chitosan, 35 mL DMF:$H_2O$ [1:1] and 1.5 eq. HCl is added and stirred at room temperature overnight to fully dissolve the chitosan. Then 4 eq. chloroacetic acid is added previously neutralized with 2 eq N,N-Diisopropylethylamine in 5 mL DMF:$H_2O$ [1:1]. After stirring for one hour at room temperature, the reaction mixture is refluxed at 60° C. followed by the drop wise addition of 2 eq. N,N-Diisopropylethylamine with the help of a syringe. After 6 hours reaction 2 eq. N,N-Diisopropylethylamine is added again. After 20 hours of heating and refluxing the reaction mixture, it is allowed to room temperature, the product is precipitated with 200 mL EtOH, and then filtered on sintered funnel. The solid is washed with excess of acetone and allowed to air dry overnight. Dialyzed against 10% NaCl solution for 3 days, followed by dialysis against pure water for 4 days. Freeze-dried to obtain the product.

The degree of -carboxymethylation (D-CM) was 14% according to $H^1$-NMR.

Example 16

In a two-necked round bottom flask, 1 g chitosan, 40 mL DMF:$H_2O$ [1:1] and 1.5 eq. HCl is added and stirred at room temperature overnight to fully dissolve the chitosan. Then 2 eq. 1-Bromo-2-(2-methoxyethoxy)-ethane (1.6 mL) is added drop wise. After stirring for one hour at room temperature, the reaction mixture is refluxed at 60° C. followed by the drop wise addition of 2 eq. N,N-Diisopropylethylamine with the help of a syringe. The reaction mixture is allowed to stir overnight. Next, 6 eq. methyl iodide (2.2 mL) was added followed by the drop wise addition of 2 eq. N,N-Diisopropylethylamine. After 20 hours of heating and refluxing the reaction mixture, it is allowed to room temperature, the product is precipitated with 200 mL EtOH, and then filtered on sintered funnel. The solid is washed with excess of acetone and allowed to air dry overnight. Dialyzed against 10% NaCl solution for 3 days, followed by dialysis against pure water for 4 days. Freeze-dried to obtain the product.

The degree of N,N,N-trialkylation in the chitosan product was 33%, the N,N-dialkylation was 48% and the N-monoalkylation was 19% according to $H^1$-NMR. The 10 degree of 2-methoxyethoxy-ethyl was estimated 65%.

Example 17

In a two-necked round bottom flask, 1 g chitosan, 40 mL DMF:$H_2O$ [1:1] and 1.5 eq. HCl is added and stirred at room temperature overnight to fully dissolve the chitosan. Then 6 eq. dimethyl sulfate added drop wise. After stirring for one hour at room temperature, the reaction mixture is refluxed at 60° C. followed by the drop wise addition of 2 eq. N,N-Diisopropylethylamine with the help of a syringe. After 6 hours reaction 2 eq. N,N-Diisopropylethylamine is added again. After 20 hours of heating and refluxing the reaction mixture, it is allowed to room temperature, the product is precipitated with 200 mL EtOH, and then filtered on sintered funnel. The solid is washed with excess of acetone and allowed to air dry overnight. Dialyzed against 10% NaCl solution for 3 days, followed by dialysis against pure water for 4 days. Freeze-dried to obtain the product.

The degree of N,N,N-trimethylation in the N-methylated chitosan product was 33% and N,N-dimethylation was 47% and N-monomethylation was 20% according to $H^1$-NMR and O-methylation was not detected.

Example 18

In a two-necked round bottom flask, 1 g chitosan, 40 mL DMF:$H_2O$ [1:1] and 1.5 eq. HCl is added and stirred at room temperature overnight to fully dissolve the chitosan. Then 2 eq. glycidyl trimethylammonium chloride is added drop wise. After stirring for one hour at room temperature, the reaction mixture is refluxed at 60° C. followed by the drop wise addition of 2 eq. N,N-Diisopropylethylamine with the help of a syringe. The reaction mixture is allowed to stir overnight. Next, 6 eq. methyl iodide was added followed by the drop wise addition of 2 eq. N,N-Diisopropylethylamine. After 20 hours of heating and refluxing the reaction mixture, it is allowed to room temperature, the product is precipitated with 200 mL EtOH, and then filtered on sintered funnel. The solid is washed with excess of acetone and allowed to air dry overnight. Dialyzed against 10% NaCl solution for 3 days, followed by dialysis against pure water for 4 days. Freeze-dried to obtain the product.

The degree of N,N,N-trialkylation in the N-methylated chitosan product was 20% and the N,N-dialkylation was 18% according to $H^1$-NMR. The degree of hydroxypropyl trimethylation was found to be 37%.

Example 19

In a two-necked round bottom flask, 1 g chitosan, 40 mL DMSO:$H_2O$ [1:1] and 1 eq. HCl is added and stirred at room temperature overnight to fully dissolve the chitosan. Then 6 eq. dimethyl sulfate is added drop wise. After stirring for 30 mins, next is the the drop wise addition of 2 eq. sodium bicarbonate in a 1M solution in $H_2O$ with the help of an addition funnel. After 24 hours reaction 2 eq. sodium bicarbonate is added again with vigorous stirring. After 48 hours at room temperature, the product is precipitated with 200 mL EtOH, and then filtered on sintered funnel. The solid is washed with excess of acetone and allowed to air dry overnight. Dialyzed against 10% NaCl solution for 3 days, followed by dialysis against pure water for 4 days. Freeze-dried to obtain the product.

The degree of N,N,N-trimethylation in the N-methylated chitosan product was 26% and N,N-dimethylation was 34% and N-monomethylation was 40% according to $H^1$-NMR.

Example 20—Analysis of NMR Spectra

Analysis of N-methyl chitosan

Figure 7:
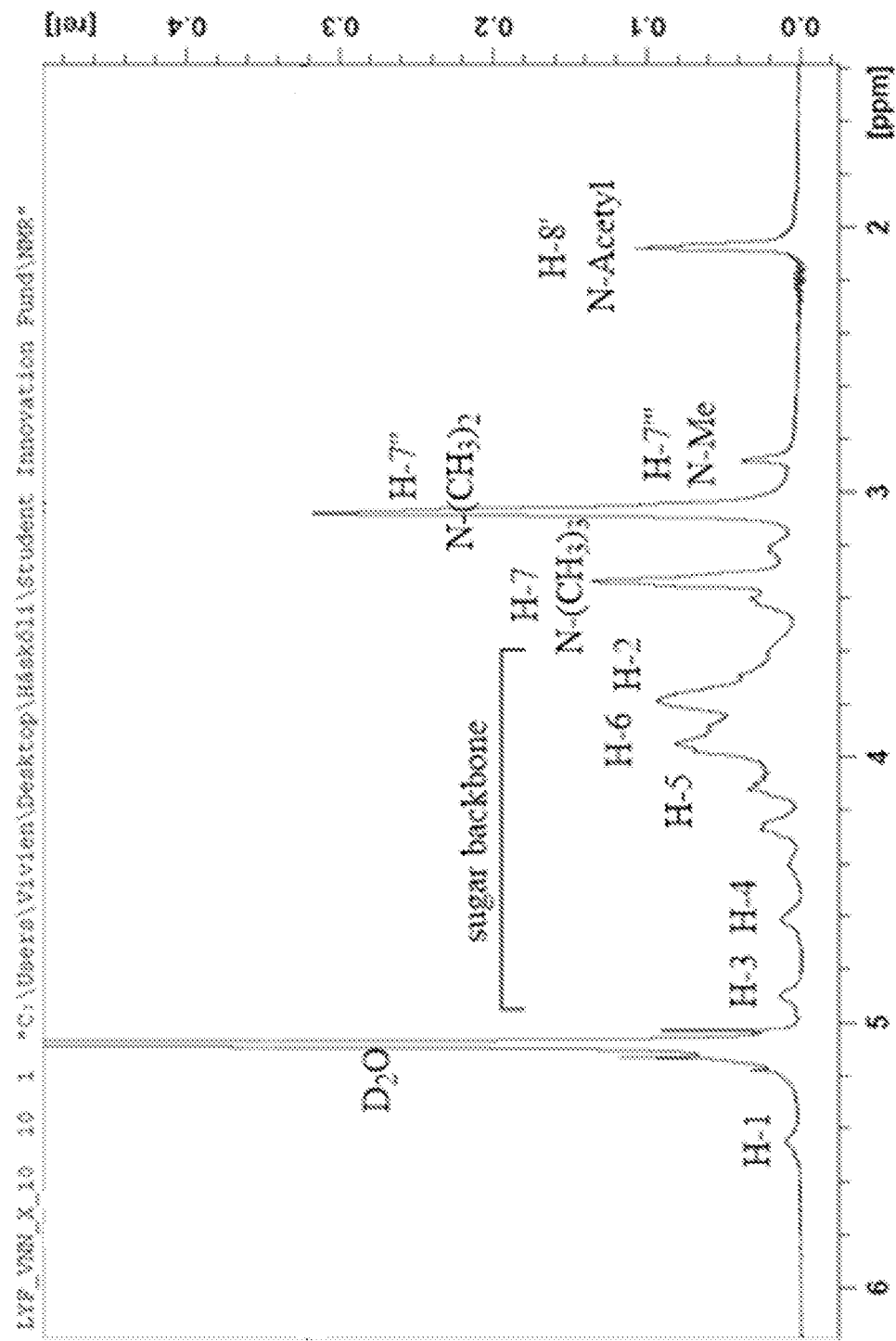
FIG. 7 shows $^1$H-NMR spectrum of TMC chitosan.

H-NMR spectroscopy was used to confirm the successful synthesis of TMC and to determine the degree of substitution. About 8-10 mg of each sample was dissolved in 0.8 mL D$_2$O and a few drops of DCI and submitted for analysis. The tri-, di- and monomethyl peaks were observed at 3.3, 3.1 and 2.9 ppm, respectively (See FIG. 7; the shift for varied from 3.33 to 3.40 for the TM peak and from 3.06-3.12 for the DM peak, due to solvent effect) and the chitosan H2-H6 peaks of chitosan backbone were observed between 4.6-3.4 ppm (The N-acetyl peak at 2.08 was used as internal reference in the spectra.). The degree of N,N,N-trimethylation (D-TM), N,N-dimethylation (D-DM) and N-monomethylation (D-MM) were calculated from the integral values by the following equations and targeted peaks as shown on FIG. 7 (the integrals for the TM, DM and MM peaks is indicated as $\int(CH_3)_3$, $\int(CH_3)_2$ and $\int CH_3$, respectively). (No O-metylation could be confirmed. It would be observed as distinct singlet peaks at 3.55 and 3.45 ppm for 3-0, and 6-0 O-methylation, respectively. A. B. Sieval, et al., Carbohyd. Polym., 36 (1998) 157-165)

$$D-TM = \frac{\frac{\int(CH3)3}{9}}{\frac{\int(CH3)3}{9} + \frac{\int(CH3)2}{6} + \frac{\int CH3}{3}} \times 100\%$$

$$D-DM = \frac{\frac{\int(CH3)2}{6}}{\frac{\int(CH3)3}{9} + \frac{\int(CH3)2}{6} + \frac{\int CH3}{3}} \times 100\%$$

$$D-MM = \frac{\frac{\int(CH3)}{3}}{\frac{\int(CH3)3}{9} + \frac{\int(CH3)2}{6} + \frac{\int CH3}{3}} \times 100\%$$

Analysis of N-ethyl chitosan

H-NMR spectroscopy was used to confirm the successful synthesis of N,N,N-triethylchitosan and to determine the degree of substitution. About 8-10 mg of each sample was dissolved in 0.8 mL D$_2$O and a few drops of acetic acid d$_4$ and submitted for analysis. The received spectra were interpreted using Topspin software (Bruker). The peaks for the N-linked CH$_2$ groups of the alkyl chain where observed 3.40 ppm in case of N,N,N-trialkylation and at 3.27 in case of N,N-dialkylaton, respectively and the chitosan H2-H6 peaks were observed between 4.6-3.4 ppm (FIG. 5). The degree of N,N,N-trialkylation (D-TA), N,N-dialkylation (D-DA) and were calculated from the integral values by the following equations: (the integrals for the TA, DA peaks is indicated as $\int(CH_2)_3$ and $\int(CH_2)_2$ respectively)

$$D-TA = \frac{\frac{\int(CH2)3}{6}}{\frac{\int(CH2)3}{6} + \frac{\int(CH2)2}{4}} \times 100\%$$

$$DDA = \frac{\frac{\int(CH2)2}{4}}{\frac{\int(CH2)3}{6} + \frac{\int(CH2)2}{4}} \times 100\%$$

Analysis of N-Hydroxypropyl N-methyl chitosan chitosan

H-NMR spectroscopy was used to confirm the successful synthesis of N-hydroxypropyl N-methyl chitosan and to determine the degree of substitution. About 8-10 mg of each sample was dissolved in 0.8 mL D$_2$O and a few drops of DCI and submitted for analysis. The N-acetyl group can be observed at 2.08 ppm. The peak for tertiary methyl groups (methyl peaks for both N, N-dimethyl and N-alkyl, N-methyl substitution) could be observed at 3.08 ppm and the peak for quaternary methyl (methyl peaks for N, N, N-trimethyl, N-alkyl, N, N-dimethyl and N, N-dialkyl, N-methyl) could be observed at 3.34 ppm. H2H6 peaks were observed between 4.6-3.4 ppm. The degree of N-hydroxypropylation (D-HP), tertiary N-methylation (D-TeM) and quaternary N-methylation (D-QM) were calculated from the integral values by the following equations: (the integrals for the protons of hydroxypropyl terminal methyl group, the quaternary ammonium methyl (as well as CH2 in the larger alkyl groups) and tertiary amine methyl (as well as CH2 larger alkyl groups) and protons H3-H6 (as well as proton H2 in acetylated monomers) indicated as $\int(CH_3)HP$, $\int(CH_3)_3$ and $\int(CHs)_2$ and $\int(H2-H6)$ respectively).

$$D-HP = \frac{\frac{\int(CH3)HP}{3}}{\frac{\int(H2-H6)}{6}} \times 100\%$$

$$D-QM = \frac{\frac{\int(CH3)3}{9}}{\frac{\int(CH3)3}{9} + \frac{\int(CH3)2}{6}} \times 100\%$$

$$D-TeM = \frac{\frac{\int(CH3)2}{6}}{\frac{\int(CH3)3}{9} + \frac{\int(CH3)2}{6}} \times 100\%$$

Analysis of N-Ethyl-N-methyl chitosan

H-NMR spectroscopy was used to confirm the successful synthesis of N-ethyl N-methyl chitosan and to determine the degree of substitution. About 8-10 mg of each sample was dissolved in 0.8 mL D$_2$O and a few drops of DCI and submitted for analysis. The peaks for the terminal CH$_3$ groups of the N-linked ethyl chain can be observed at 1.38 ppm. The N-acetyl group can be observed at 2.07 ppm. The peak for tertiary methyl groups (methyl peaks for both N, N-dimethyl and N-alkyl, N-methyl substitution) could be observed at 3.08 ppm and the peak for quaternary methyl (methyl peaks for N, N, N-trimethyl, N-alkyl, N, N-dimethyl and N, N-dialkyl, N-methyl) could be observed at 3.34 ppm. H2—H6 peaks were observed between 4.6-3.4 ppm. The degree of N-ethylation (D-ET), quaternary N-methylation (D-QM and tertiary N-methylation (D-TeM)) were calculated from the integral values by the following equations: (the integrals for the ethyl terminal methyl group, the quaternary methyl groups and tertiary methyl groups and protons H3-H6 (as well as proton H2 in acetylated monomers) was indicated as $\int(CH_3)Et$, and $\int(CH_3)_3$, $\int(CH_3)_2$ and $\int(H3-H6)$ respectively).

$$D\text{-}TE = \frac{\frac{\int(CH3)Et}{3}}{\frac{\int(H2-H6)}{6}} \times 100\%$$

$$D\text{-}QM = \frac{\frac{\int(CH3)3}{9}}{\frac{\int(CH3)3}{9} + \frac{\int(CH3)2}{6} + \frac{\int CH3}{3}} \times 100\%$$

$$D\text{-}TeM = \frac{\frac{\int(CH3)2}{6}}{\frac{\int(CH3)3}{9} + \frac{\int(CH3)2}{6} + \frac{\int CH3}{3}} \times 100\%$$

Analysis of N-2-(2-methoxyethoxy)-ethyl-N-methyl chitosan

H-NMR spectroscopy was used to confirm the successful synthesis of N-2-(2-methoxyethoxy)-ethyl-N-methyl chitosan and to estimate the degree of substitution. About 8-10 mg of each sample was dissolved in 0.8 mL D$_2$O and a few drops of DCI and submitted for analysis. The N-acetyl group can be observed at 2.07 ppm. The peak for tertiary methyl groups (methyl peaks for both N, N-dimethyl and N-alkyl, N-methyl substitution) could be observed at 3.08 ppm and the peak for quaternary methyl (methyl peaks for N, N, N-trimethyl, N-alkyl, N, N-dimethyl and N, N-dialkyl, N-methyl) could be observed at 3.37. ppm.H2—H6 peaks were observed between 4.6-3.4 ppm. and overlapped with the methoxy and ethoxy peaks. (the integral is indicated as $\int$ppm 4.6-3.4 and other integrals indicated as before) The tertiary N-methylation (D-TeM) and quaternary N-methylation (D-QM) and was estimated from the integral values by the following equations:

$$D\text{-}TQ = \frac{\frac{\int(CH3)3}{9}}{\frac{\int(CH3)3}{9} + \frac{\int(CH3)2}{6} + \frac{\int(CH3)}{3}} \times 100\%$$

$$D\text{-}TeM = \frac{\frac{\int(CH3)2}{6}}{\frac{\int(CH3)3}{9} + \frac{\int(CH3)2}{6} + \frac{\int(CH3)}{3}} \times 100\%$$

The degree of 2-methoxyethoxy-ethyl was estimated from the total integral of peaks in the range 4.6-3.4 ppm.

$$D\text{-}MEE = \frac{\int ppm 4.6 - 3.4 - \left(\frac{\int(CH3)3}{9} + \frac{\int(CH3)2}{6} + \frac{\int(CH3)}{3}\right) - 6}{11} \times 100\%$$

Analysis of N-(2-hydroxy)propyl-3-trimethyl ammonium)-N-methyl chitosan

H-NMR spectroscopy was used to confirm the successful synthesis of N-ethyl N-methyl chitosan and to determine the degree of substitution. About 8-10 mg of each sample was dissolved in 0.8 mL D$_2$O and a few drops of DCI and submitted for analysis. The peaks for the quaternary N—CH$_3$ groups of the N-linked 2-hydroxypropyl-3-trimethyl ammonium moiety can be observed at 3.28 ppm. The N-acetyl group can be observed at 2.07 ppm. The peak for tertiary methyl groups (methyl peaks for both N, N-dimethyl and N-alkyl, N-methyl substitution) could be observed at 3.08 ppm and the peak for quaternary methyl (methyl peaks for N, N, N-trimethyl, N-alkyl, N, N-dimethyl and N, N-diallkyl, N-methyl) could be observed at 3.35 ppm. H2—H6 peaks were observed between 4.6-3.4 ppm. The degree of substitution N-hydroxpropyl 2-hydroxy)propyl-3-trimethyl ammonium (D-HPTM), tertiary N-methylation (D-TeM) and quaternary N-methylation (D-QM) and were calculated from the integral values by the following equations: (the integrals for the HPTM trimethylgroup, quaternary methyl groups the tertiary methyl groups and was indicated as $\int(CH3)3$-HPTM, $\int(CH3)3$ and $\int(CH3)$ respectively).

$$D\text{-}HPTM = \frac{\frac{\int(CH3)3 - HPTM}{9}}{\frac{\int(CH3)3}{9} + \frac{\int(CH3)2}{6}} \times 100\%$$

$$D\text{-}TQ = \frac{\frac{\int(CH3)3}{9}}{\frac{\int(CH3)3}{9} + \frac{\int(CH3)2}{6}} \times 100\%$$

$$D\text{-}TeM = \frac{\frac{\int(CH3)2}{6}}{\frac{\int(CH3)3}{9} + \frac{\int(CH3)2}{6}} \times 100\%$$

Analysis of CMC Chitosan

H-NMR spectroscopy was used to confirm the successful synthesis of CMC and to determine the degree of substitution. About 8-10 mg of each sample was dissolved in 0.8 mL D$_2$O and a few drops of DCI and submitted for analysis. The chitosan H2—H6 peaks of chitosan backbone were observed between 4.04-3.04 ppm. The N-acetyl peak at 2.08 was used as internal reference in the spectra. The protons for N linked CH₂ of the carboxymethyl group were observed at 4.23 ppm. The degree of carboxymethylation (D-CM) was calculated from the integral values by the following equation:

$$D\text{-}CM = \frac{\dfrac{\int (CH3) - CM}{2}}{\dfrac{\int (H2 - H6)}{6}} \times 100\%$$

The invention claimed is:

1. A compound having the formula

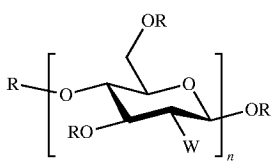
(I)

wherein n is an integer greater than or equal to 3, wherein W is N-acetyl:

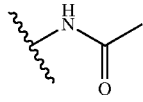

in from 0 to 70% of monomer units and where W is not N-acetyl it is a group selected from:

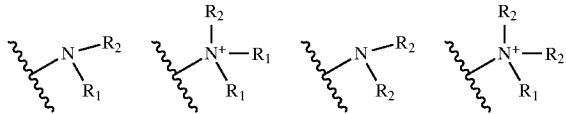

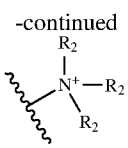

wherein each $R_1$ substituent is independently selected from H, $CH_3$, and —$(CH2)_a$—$CH_3$, wherein a is from 1 to 22, provided that when $R_1$ is present it is not H in at least 10% of monomer units, and wherein $R_2$ is selected from:

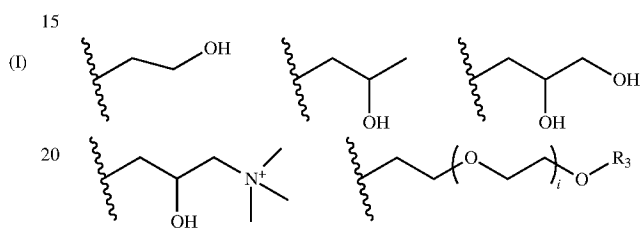

wherein i is an integer from 1-200, and $R_3$ is selected from H, —$(CH_2)_j$—$CH_3$ and —CO—$(CH_2)_j$—$CH_3$, wherein j is 0, 1, 2, 3, 4, or 5, wherein R is H in at least 75% of the total number of positions, and when it is not H, R is the same as amino substituent $R_1$ or $R_2$ in W;

or a salt thereof.

2. The compound according to claim 1, wherein when $R_1$ is present in W, it is not H in at least 20% of monomer units.

3. The compound according to claim 1, wherein R is H.

4. The compound according to claim 1, wherein W comprises trisubstituted N.

5. The compound according to claim 4 having a counterion selected from Cl⁻, Br⁻, and $CH_3OSO_2O^-$.

* * * * *